US012680206B2

(12) United States Patent
Baharlou et al.

(10) Patent No.: US 12,680,206 B2
(45) Date of Patent: *Jul. 14, 2026

(54) PORTABLE SPINNER AND METHODS OF USE

(71) Applicant: Temple University—Of The Commonwealth System of Higher Education, Philadelphia, PA (US)

(72) Inventors: Sogol M. Baharlou, Philadelphia, PA (US); Jonathan A. Gerstenhaber, Philadelphia, PA (US); Yah-el H. Har-el, Philadelphia, PA (US); Peter I. Lelkes, Cherry Hill, NJ (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 65 days.

This patent is subject to a terminal disclaimer.

(21) Appl. No.: 18/751,834

(22) Filed: Jun. 24, 2024

(65) Prior Publication Data

US 2025/0019879 A1      Jan. 16, 2025

Related U.S. Application Data

(63) Continuation of application No. 15/764,476, filed as application No. PCT/US2016/054410 on Sep. 29, 2016, now Pat. No. 12,031,252.

(60) Provisional application No. 62/335,212, filed on May 12, 2016, provisional application No. 62/256,485, filed on Nov. 17, 2015, provisional application No. 62/234,270, filed on Sep. 29, 2015.

(51) Int. Cl.
    *D01F 1/10* (2006.01)
    *D04H 1/728* (2012.01)
    *D01D 5/00* (2006.01)
    *D01D 5/14* (2006.01)

(52) U.S. Cl.
    CPC ............... *D04H 1/728* (2013.01); *D01F 1/10* (2013.01); *A61L 2400/12* (2013.01); *D01D 5/003* (2013.01); *D01D 5/0061* (2013.01); *D01D 5/14* (2013.01); *D10B 2509/00* (2013.01)

(58) Field of Classification Search
    CPC ............................... D01D 5/003; D04H 1/728
    See application file for complete search history.

(56) References Cited

U.S. PATENT DOCUMENTS 12,031,252 B2 * 7/2024 Baharlou ............... D04H 1/728
2016/0287227 A1 * 10/2016 Zaballa ............... D01D 5/0069

FOREIGN PATENT DOCUMENTS

WO      WO-2016126201      *  8/2016

* cited by examiner

*Primary Examiner* — Alison L Hindenlang
*Assistant Examiner* — Debjani Roy
(74) *Attorney, Agent, or Firm* — Riverside Law LLP

(57) ABSTRACT

The present invention provides portable devices and systems for electrofocused blow spinning, and methods for using the same. The devices of the invention are convenient to carry and use and are able to aerodynamically spin a variety of materials in a mobile setting.

27 Claims, 12 Drawing Sheets

PORTABLE SPINNER AND METHODS OF USE

CROSS-REFERENCE TO RELATED APPLICATIONS

This application is a continuation of U.S. application Ser. No. 15/764,476, filed Mar. 29, 2018, which is a U.S. national phase application filed under 35 U.S.C. § 371 claiming benefit to International Patent Application No. PCT/US16/ 54410, filed Sep. 29, 2016, which is entitled to priority under 35 U.S.C. § 119(e) to U.S. Provisional Patent Application No. 62/234,270 filed Sep. 29, 2015; U.S. Provisional Patent Application No. 62/256,485 filed Nov. 17, 2015; and U.S. Provisional Patent Application No. 62/335,212 filed May 12, 2016, the contents of which are each incorporated herein by reference in their entirety.

BACKGROUND OF THE INVENTION

The technique of blow spinning liquids and/or solutions capable of forming fibers, is well known and has been described in a number of patents as well as in the general literature.

For example, U.S. Pat. No. 8,641,960 describes a method for producing micro and nanofibers from a polymer solution. The method uses a compound nozzle with at least one internal concentric nozzle, whereby the simultaneous ejection of polymer solution from the internal nozzle with ejection of a pressurized gas from the external nozzle produces polymer fibers that may be collected on a target. However, the prior art depicts a bulky blow spinning device, and rules out the use of electricity, such as in biological applications.

In another example, U.S. Patent Publication No. 2005/ 0073075 describes a method for industrial-scale electroblowing of fibers onto a collector. The method uses a series of spinnerets and gas orifices to eject polymer streams into an electric field. However, the prior art is also dependent on bulky machinery to produce the fibers, and the electric field is dependent on an array of electrodes generating an electrostatic differential between the spinnerets and the collector.

There is a need in the art for improved devices and methods for portable, rapid fabrication of fibers, for applications such as on demand fabrication of wound dressings regardless of the size or depth of the wound. The present invention meets this need.

SUMMARY OF THE INVENTION

The present invention provides portable devices and systems for electrofocused blow spinning (EFBS), and methods for using the same. The devices of the invention are convenient to carry and use and are able to aerodynamically spin a variety of materials.

In one aspect, the invention relates to a handheld electrofocused blow spinning (EFBS) device, comprising: a spinneret comprising an outer sheath and an inner needle; a syringe, capable of holding spinning solution, fluidly connected to the spinneret inner needle; at least one gas regulator; and a gas supply fluidly connected to the syringe and the spinneret outer sheath, such that the gas supply is capable of simultaneously pressurizing the syringe and propelling gas out of the spinneret outer sheath.

In one embodiment, the inner needle is electrically conductive. In one embodiment, the device further comprises a power source and a high voltage power supply. In one embodiment, the power source and the high voltage power supply are electrically connected to the inner needle. In one embodiment, the gas supply comprises a pressurized cartridge of gas. In one embodiment, the gas is selected from the group consisting of $CO_2$, $N_2$, NO, and air. In one embodiment, the gas supply comprises an air pump. In one embodiment, the pump is selected from the group consisting of a syringe pump, a peristaltic pump, a diaphragm pump, and a vane pump. In one embodiment, the spinning solution comprises a plant protein, an animal protein, a synthetic polymer, or any combination thereof. In one embodiment, the plant protein comprises water-soluble soy protein, or a bioactive component thereof. In one embodiment, the spinning solution further comprises a high-molecular weight polymer. In one embodiment, the high-molecular weight polymer is polyethylene oxide.

In another aspect, the invention relates to a method of dressing a wound in a subject, the method comprising the steps of: loading a syringe with a wound dressing solution; connecting the syringe to a syringe adapter and a tube that is fluidly connected to a spinneret comprising an outer sheath and an inner needle; providing a flow of gas through the outer sheath of the spinneret; providing a flow of gas to the syringe adapter to dispense the wound dressing solution through the inner needle of the spinneret; and spinning the wound dressing solution onto a wound surface.

In one embodiment, a voltage is provided to the inner needle of the spinneret. In one embodiment, the wound dressing solution comprises a plant protein, an animal protein, a synthetic polymer, or any combination thereof. In one embodiment, the plant protein comprises water-soluble soy proteins, or a bioactive component thereof. In one embodiment, the wound dressing solution further comprises a high-molecular weight polymer. In one embodiment, the high-molecular weight polymer is polyethylene oxide. In one embodiment, the gas is selected from the group consisting of $CO_2$, $N_2$, NO, and air. In one embodiment, the flow of gas through the outer sheath of the spinneret has a pressure between 3 and 5 psi. In one embodiment, the dispensation of wound dressing solution through the inner needle of the spinneret has a flow rate of 1.5 mL/hr.

In another aspect, the invention relates to a method of repairing a compromised material surface, the method comprising the steps of: loading a syringe with a repair solution; connecting the syringe to a syringe adapter and a tube that is fluidly connected to a spinneret comprising an outer sheath and an inner needle; providing a flow of gas through the outer sheath of the spinneret; providing a flow of gas to the syringe adapter to dispense the repair solution through the inner needle of the spinneret; and spinning the repair solution onto the compromised material surface. In one embodiment, the compromised material surface is not electrically charged.

In another aspect, the invention relates to a method of preparing a fabric on a surface, the method comprising the steps of: loading a syringe with a spinning solution; connecting the syringe to a syringe adapter and a tube that is fluidly connected to a spinneret comprising an outer sheath and an inner needle; providing a flow of gas through the outer sheath of the spinneret; providing a flow of gas to the syringe adapter to dispense the spinning solution through the inner needle of the spinneret; spinning the repair solution onto the surface to form a fabric; and separating the fabric from the surface. In one embodiment, the method further comprises a step of treating the fabric in a vacuum oven.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2 depicts another perspective view of the exemplary EFBS depicted in FIG. 1.

DETAILED DESCRIPTION

Figure 1:
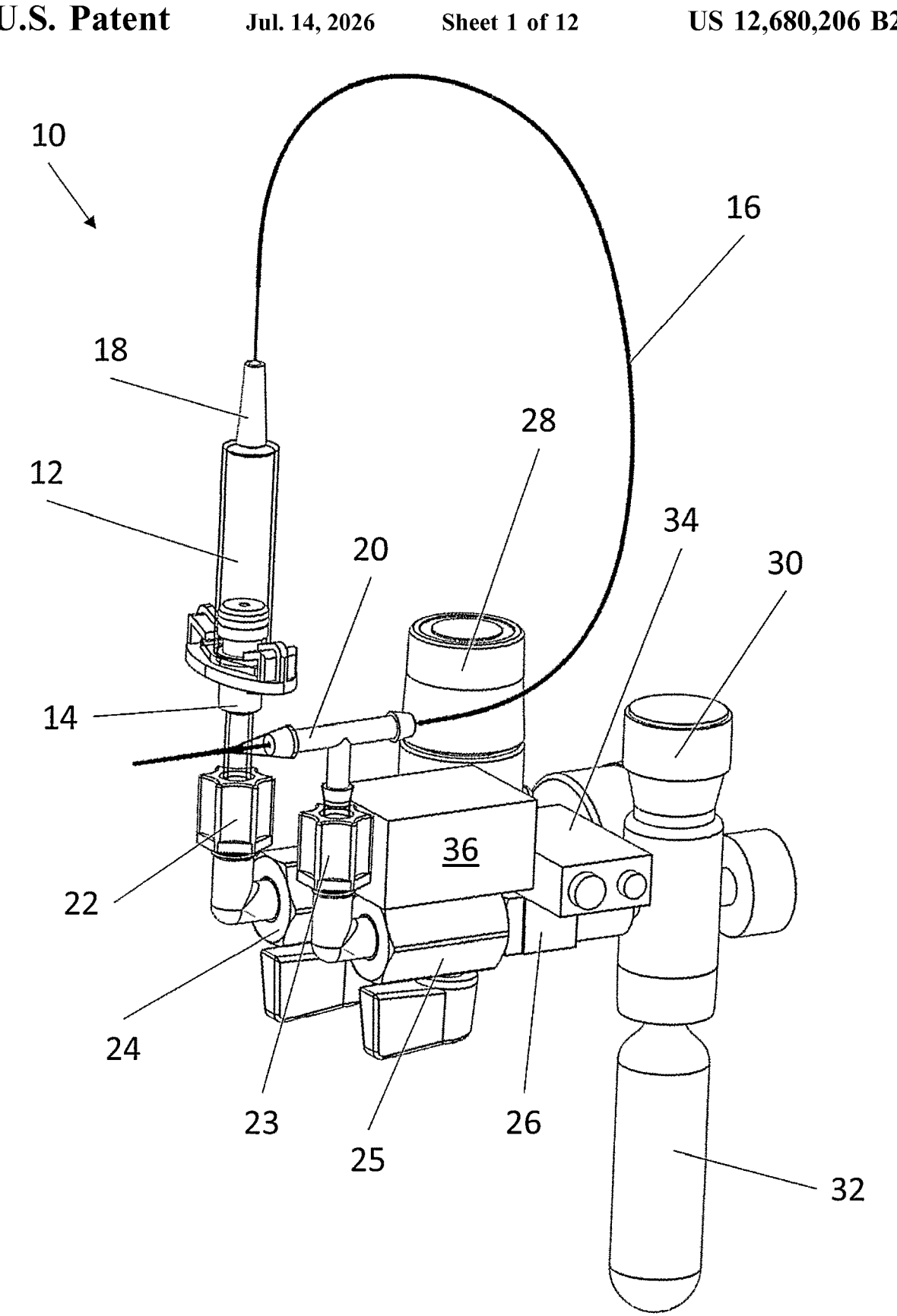
FIG. 1 depicts a perspective view of an exemplary hand-held electrofocused blow spinner (EFBS).

The present invention provides portable electrofocused blow spinning (EFBS) devices, systems, and methods for using the same. The devices of the invention are convenient to carry and use in clinical/physician's office setting and are able to aerodynamically spin non-woven fabric-like structures out of a variety of materials, such as, but not limited to plant or animal protein and synthetic polymers in a mobile setting.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20%, +10%, +5%, +1%, and +0.1% from the specified value, as such variations are appropriate.

As used herein, the term "dressing" refers broadly to materials when prepared for, and applied to, a wound for protection, absorbance, drainage, etc.

The term "blow spinning" refers to methods wherein materials are streamed, sprayed, sputtered or dripped toward a target substrate. The materials can be aerodynamically guided in the direction of a target substrate by one or more sources of pressurized gas streams.

The term "electrofocused" blow spinning refers to blow spinning methods wherein an electric field is provided solely to improve the focusing of a material stream towards a target substrate, rather than a necessary element to generate a stream of polymer such as in electrospinning. The term "electrofocused" is not limited to the specific examples set forth herein, and it includes any means of using an electrical field for depositing a material on a target.

As used herein, the term "wound" is used to refer broadly to injuries to the skin and subcutaneous tissue initiated in different ways (e.g., pressure sores from extended bed rest and wounds induced by trauma) and with varying characteristics. Wounds are generally classified into one of four grades depending on the depth of the wound: Grade I: wounds limited to the epithelium; Grade II: wounds extending into the dermis; Grade III: wounds extending into the subcutaneous tissue; and Grade IV (or full-thickness wounds), which are wounds in which bones are exposed (e.g., a bony pressure point such as the greater trochanter or the sacrum).

As used herein, the phrases "promote wound healing," "enhance wound healing," and the like refer to processes that augment the natural process of wound healing, and may comprise the induction of the formation of granulation tissue of wound contraction, the induction of epithelialization (i.e., the generation of new cells in the epithelium), regeneration of skin appendages, such as hair follicles and sweat glands, or merely the protection of a wound from infection or further injury, or all of the above in various combinations.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Figure 2:
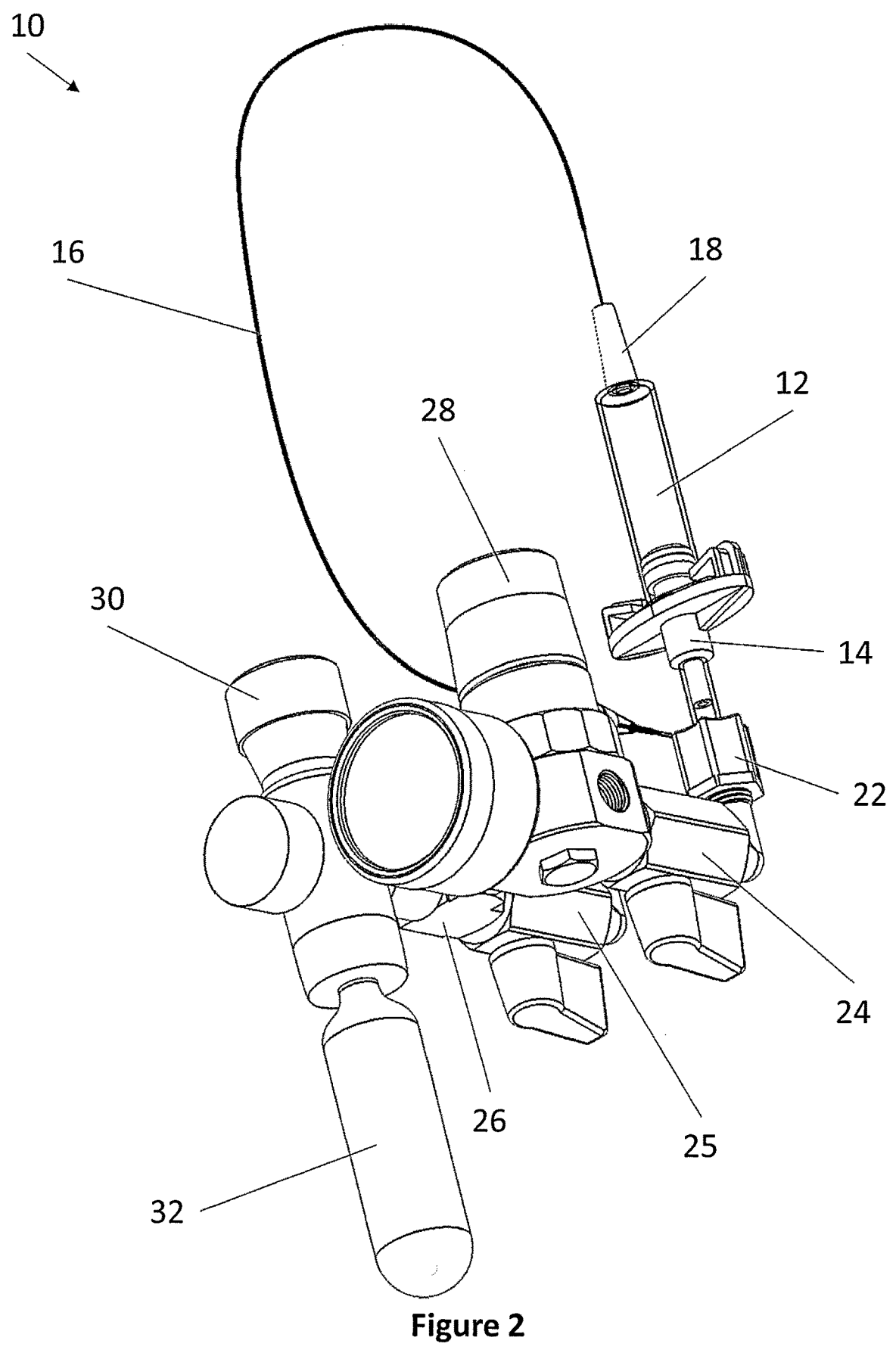

Handheld EFBS Device Referring now to FIG. 1 and FIG. 2, isometric views of an exemplary handheld electrofocused blow spinning (EFBS) device 10 is depicted. Handheld EFBS device 10 comprises syringe 12 for holding spinning solution. The spinning solution can comprise any suitable solution, depending on its use. For example, if the use is for creating non-woven polymer fabrics, the spinning solution can be any natural or synthetic polymers dissolved in an aqueous or organic solvent. In another example, if the use is for creating non-woven wound dressings, the spinning solution can comprise bioactive or non-bioactive compounds such as natural or synthetic polymers or macromolecules dissolved in an aqueous or organic solvent. Non-limiting examples of solvents include: N,N-Dimethyl formamide (DMF), tetrahydrofuran (THF), methylene chloride, dioxane, ethanol, hexafluoroisopropanol (HFIP), chloroform, glacial acetic acid, water, and combinations thereof. In various embodiments, any solvents may also be used as co-solvents. Syringe 12 is attached to handheld EFBS device 10 and actuated by syringe adapter 14. Syringe 12 is fluidly connected to tube 16 to dispense the spinning solution to spinneret 20. In some embodiments, syringe 12 is tipped with needle 18 to facilitate the fluid connection to tube 16. Syringe 12 and needle 18 can be any suitable size. In various embodiments, the size of syringe 12 and needle 18 will depend on the amount of spinning solution to be dispensed. In certain embodiments, syringe 12, needle 18, tube 16, or any combinations thereof are easily removable for purposes of changing spinning solution, refilling spinning solution, cleaning the components, or replacing the components.

Syringe adapter 14 is attached to handheld EFBS device 10 by first compression fitting 22 and first valve 24. Spinneret 20 is attached to handheld EFBS device 10 by second compression fitting 23 and second valve 25. First valve 24 and second valve 25 can be any suitable valve that provides an airtight fit, such as a ball valve, a globe valve, a pinch valve, a needle valve, and the like. First compression fitting 22 and second compression fitting 23 can be any suitable fitting that releasably and fluidly joins two lumens, such as a push-to-connect fitting, a quick-disconnect fitting, a threaded fitting, and the like. Compression fittings allow for releasable airtight connections, and valves provide an adjustable airtight fit to reduce the loss of pressurized gas. These features facilitate the connection and disconnection of entire fluid paths, allowing for quick and simple interchanging of parts to suit material use and application. Cartridge 32 comprises a source of portable pressurized gas and is loaded into cartridge regulator 30. Cartridge 32 can comprise any suitable pressurized gas, preferably an inert gas or a biologically compatible gas. Non-limiting examples of pressurized gas include $CO_2$, $N_2$, NO, ambient air, and the like. Cartridge regulator 30 controls the output of pressurized gas from cartridge 32. In some embodiments, handheld EFBS device 10 comprises a single cartridge 32. A single cartridge 32 provides a split source of pressurized gas to all of the components of handheld EFBS device 10. For example, in FIG. 1 and FIG. 2, a handheld EFBS device 10 comprises fitting 26 connected to cartridge regulator 30 and splits the gas flow to simultaneously propel solution out of spinneret 20 and to drive syringe 12. For example, a first flow of gas is directed to second valve 25 to dispense gas through spinneret 20. A second flow of gas is directed to gas regulator 28 to dispense gas into syringe adapter 14, wherein the gas pressure drives the plunger of syringe 12 to dispense the spinning solution within. In other embodiments, handheld EFBS device 10 comprises a plurality of cartridges (not shown). For example, a handheld EFBS device may comprise a cartridge for each element that is drivable by pressurized gas. Each cartridge may comprise additional fittings, gas lines, and valves for independently driving, e.g., a syringe adapter and a spinneret. Each cartridge may also comprise additional gas regulators for separately controlling the outputs of pressurized gas. In various embodiments, the handheld EFBS device may comprise one or more controllers for receiving inputs and automating the various electrical components.

Figure 3:
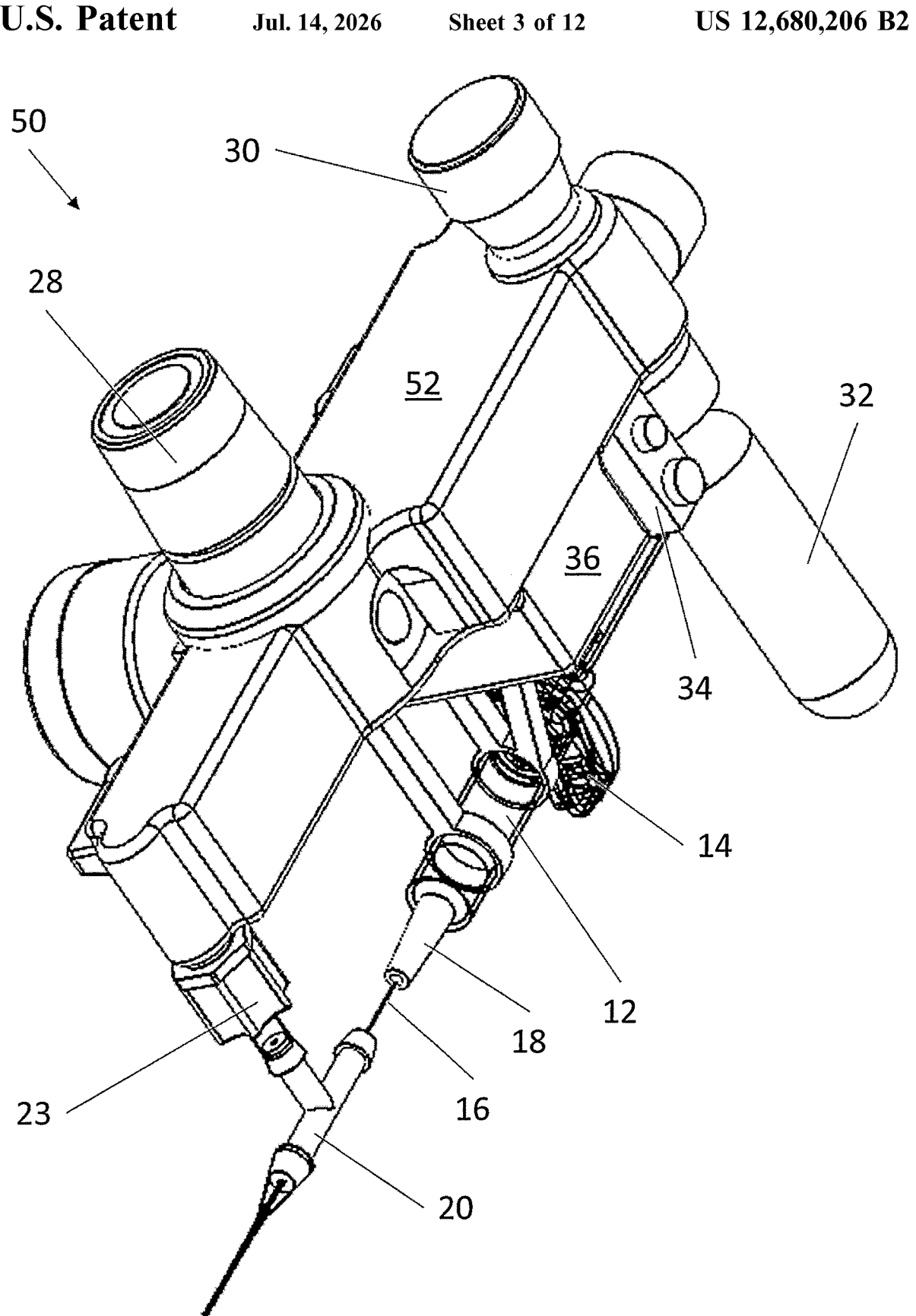
FIG. 3 depicts a perspective view of another exemplary EFBS.
Figure 4:
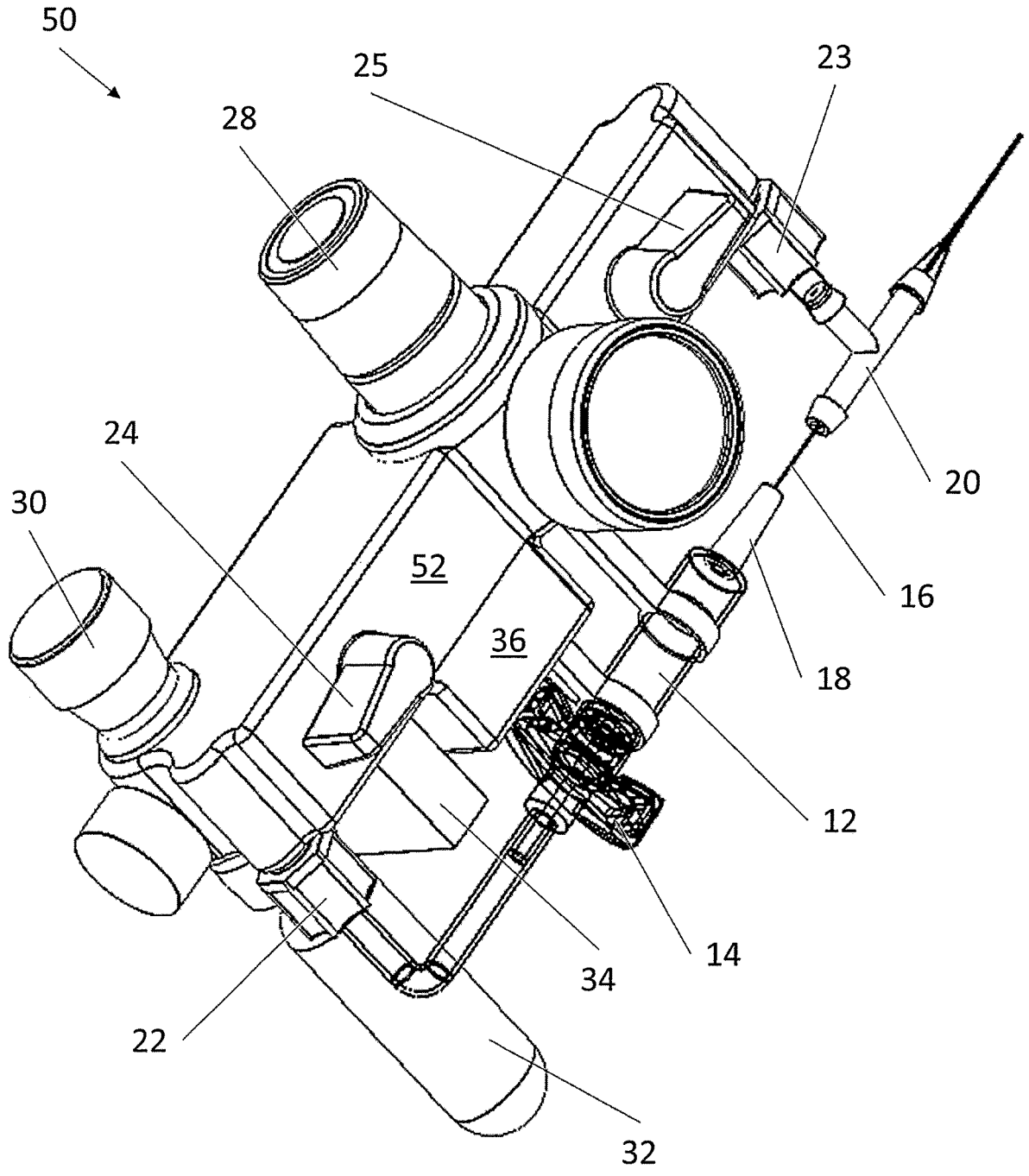
FIG. 4 depicts another perspective view of the exemplary EFBS depicted in FIG. 3.

Referring now to FIG. 3 and FIG. 4, handheld EFBS device 50 is depicted. Handheld EFBS device 50 comprises an alternative layout of the components of handheld EFBS device 10. Handheld EFBS device 50 features a rearrangement of gas regulator 28 to dispense gas into spinneret 20, and of cartridge regulator 30 to dispense gas into syringe adapter 14 to drive the plunger of syringe 12 and dispense the spinning solution within. Handheld EFBS device 50 also features an additional enclosure 52, which covers certain parts including first valve 24, second valve 25, and fitting 26. In some embodiments, the handheld EFBS devices of the present invention comprise a powered pump, such as a powered positive displacement air pump (not shown). A powered positive displacement air pump provides an alternative source of gas flow that can utilize ambient air to drive the components of the handheld EFBS devices of the present invention instead of relying on a pressurized cartridge. Non-limiting examples of positive displacement air pumps include syringe pumps, peristaltic pumps, diaphragm pumps, and vane pumps.

Figure 5:
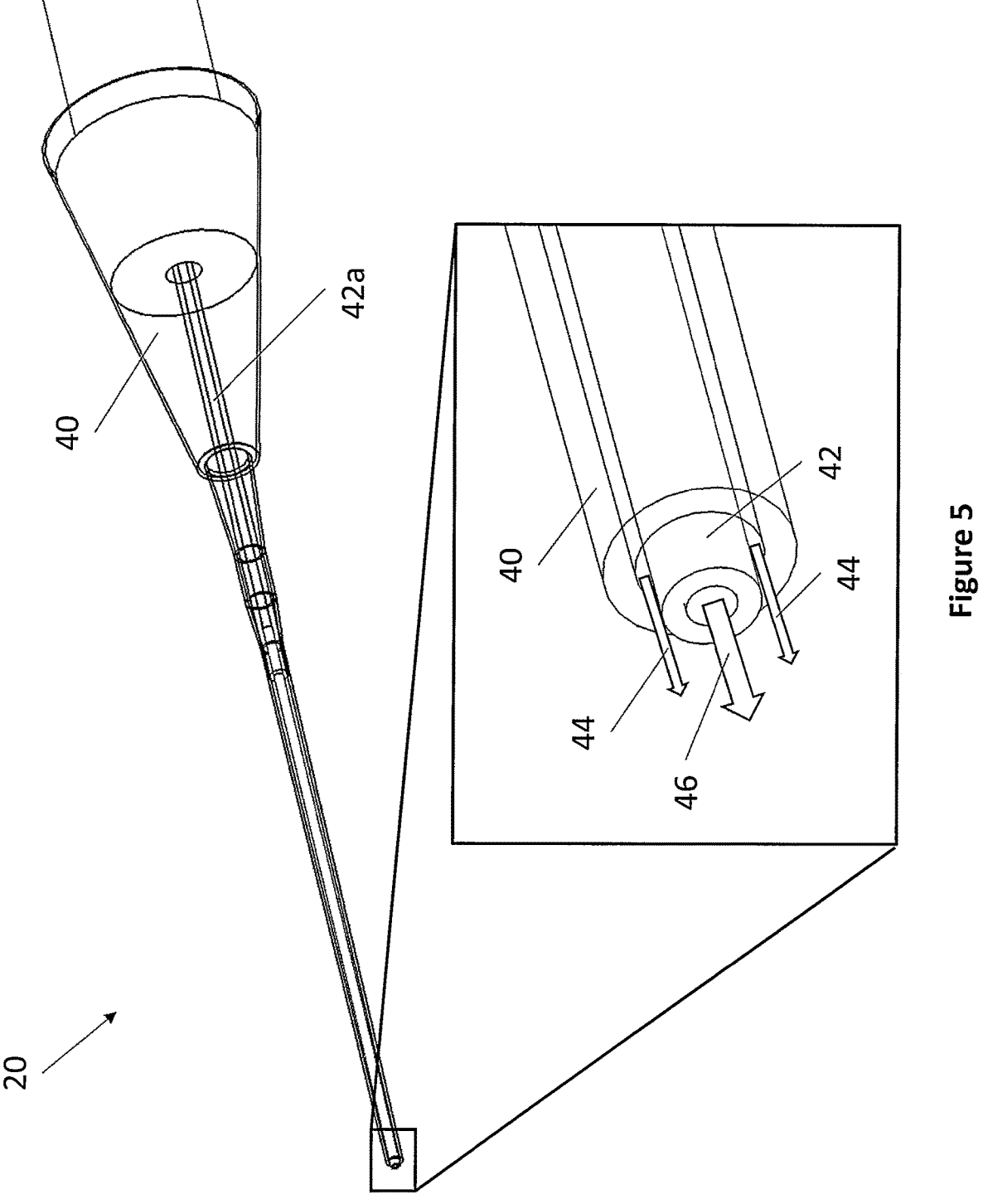
FIG. 5 depicts an exemplary spinneret construction and flow of gas and spinning solution.

Referring now to FIG. 5, a magnified view of spinneret 20 is depicted. Spinneret 20 comprises outer sheath 40 and inner needle 42. In some embodiments, the tip of inner needle 42 extends past the opening of outer sheath 40. For example, the tip of inner needle 42 can extend 1 mm past the opening of outer sheath 40. In other embodiments, the distance between the tip of inner needle 42 and outer sheath 40 is adjustable. Outer sheath 40 and inner needle 42 can comprise any suitable size and shape. For example, in some embodiments, the diameter of the opening of outer sheath 40 can be between 0.5 and 2.5 mm, and the size of inner needle 42 can be between 20 and 30 gauge. It should be understood that varying the size and shape will vary the operability of the handheld EFBS devices of the present invention. For example, larger diameters may provide greater flow but will also require a larger power output and volume of gas, and variable widths and shapes of the openings may provide manipulability in gas flow dynamics over the dispensed solution as desired. Outer sheath 40 can comprise any suitable material. For example, outer sheath 40 can comprise plastics, glass, metals, and the like. Inner needle 42 can comprise any suitable material, such as a metal or a plastic. In some embodiments, inner needle 42 comprises an electrically conductive material. Inner needle 42 is fluidly connected to tube 16 and provides for spinning solution flow 46 through its lumen. In some embodiments, inner needle 42 can be nonconductive, such as in the context of a non-electric blow spinning device. Outer sheath 40 is fluidly connected to pressurized gas from cartridge 32 and provides for gas flow 44 through its lumen. In various embodiments, outer sheath 40 and inner needle 42 are easily removable for purposes of changing part width and length, cleaning the components, or replacing the components. In some embodiments, wherein cost effectiveness or wide availability of components is desired, outer sheath 40 can comprise typical pipette tips and inner needle 42 can comprise typical cannulated needles.

In certain embodiments, spinneret 20 further comprises inner needle 42a. Inner needle 42a is fluidly connected to inner needle 42 and provides a lumen bridging the spinning fluid pathway between tube 16 and inner needle 42. In some embodiments, inner needle 42a and inner needle 42 are connected by a length of polymer tube. Inner needle 42a is preferably not exposed to the exterior of spinneret 20, such that no user contact may be made with inner needle 42a during use of the device. Inner needle 42a may then be connected to a high voltage supply to provide a spinning fluid stream with a charge, while protecting a user from directly contacting any exposed electrically powered part.

In certain embodiments, the handheld EFBS devices of the present invention further comprise power source 34 and high voltage power supply 36. Power source 34 provides electricity to high voltage power supply 36, and can comprise any suitable portable source of power, such as a battery. High voltage power supply 36 accepts electricity from power source 34 and outputs electricity at high voltage. For example, the voltage output can be between 100V and 30 kV. In certain embodiments, the voltage output from high voltage power supply 36 is electrically connected to inner needle 42, such that a high voltage may be applied to spinning solution flow 46. In other embodiments, power source 34 may also provide power to additional components, such as an electric pump.

It should be appreciated that the handheld EFBS devices of the present invention are small, lightweight, and portable for easy transport and use in any location, such as in the field. The small size and weight allows operators to manipulate the devices with one hand or two hands. Due to the devices' portability and ease of use, an operator may directly handle the devices to deposit electrofocused blow-spun materials onto any surface, such as wounds or skin. In various embodiments, the handheld EFBS devices of the present invention comprise additional features for ease of use and handling. For example, the handheld EFBS devices may further comprise a handle or a grip to enable a user to comfortably hold and direct the spinneret. Other features may include enclosures or housings that at least partially encase the device as desired to improve aesthetics, durability, and comfort. The enclosures or housings may include one or more slots for easily engaging and disengaging the various portable and exchangeable components of the handheld EFBS devices, such as a portable power source, a portable syringe, and a portable gas cartridge.

It should be appreciated that the devices encompassed by the present invention are not limited to the particular embodiments depicted in FIG. 1 through FIG. 5. Rather, devices within the scope of the present invention may comprise the components disclosed herein arranged in any number of suitable configurations. Devices within the scope of the present invention may further comprise additional components such as digital readouts, flow sensors, pressure sensors, voltmeters, and the like.

Methods of Use

The invention provides paradigmatic methods for using the handheld EFBS devices of the present invention. The methods use the handheld EFBS devices to dispense a non-woven fabric-like structure onto a surface, such as a wound, for enhanced wound healing. The methods are particularly advantageous in situations where rapid deployment of a flexible wound coating cannot be accomplished with premade wound dressings.

Figure 6:
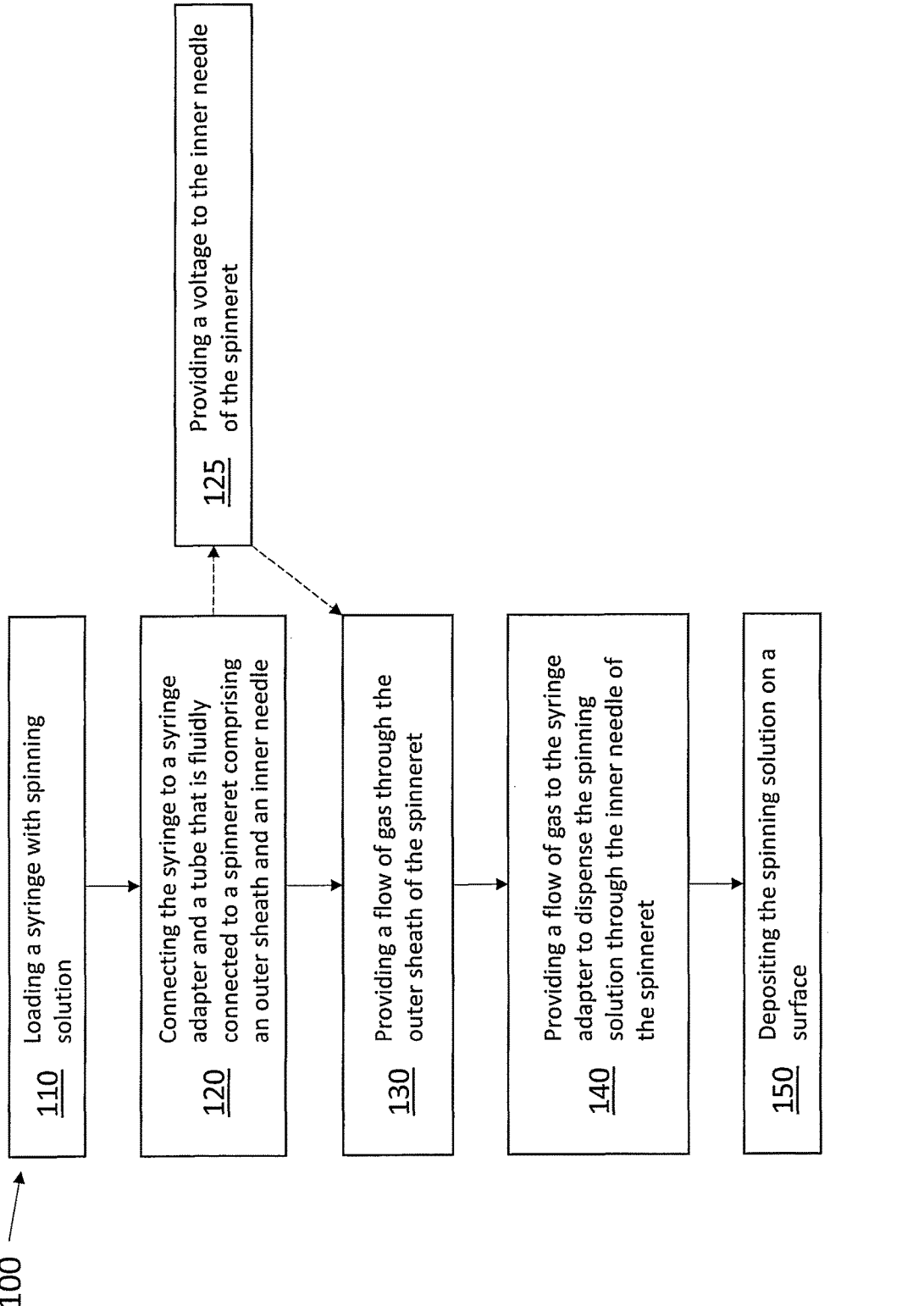
FIG. 6 depicts an exemplary method using a handheld EFBS.

Referring now to FIG. 6, an exemplary method 100 for the portable deposition of a spinning solution onto a surface is provided. Method 100 begins with step 110, wherein a syringe is loaded with spinning solution. The spinning solution can be any suitable solution, selected based on the composition of the desired non-woven fabric-like structure. In step 120, the syringe is connected to a syringe adapter and to a tube that is fluidly connected to a spinneret comprising an outer sheath and an inner needle. Optionally in step 125, a voltage is provided to the inner needle of the spinneret. In step 130, a flow of gas is provided through the outer sheath of the spinneret. In step 140, a flow of gas is provided to the syringe adapter to dispense the spinning solution through the inner needle of the spinneret. In step 150, the spinning solution is deposited onto a surface. Upon leaving the spinneret, the spinning solution is reduced to fibers ranging from under 1 micron to a couple microns in diameter.

In some embodiments, the method provides for the portable deposition of a solute-water mixture onto a wound as a wound dressing. The solute can be any suitable solute, such as plant-derived water-soluble proteins including highly-purified water-soluble soy protein isolate (WSsoy). The WSsoy mixture can comprise any suitable WSsoy amount, such as a range between 1% and 80% by weight. In certain embodiments, the WSsoy mixture may comprise between 5% and 25% WSsoy by weight. In one embodiment, the WSsoy mixture may comprise WSsoy at 8% weight. In another embodiment, the WSsoy mixture may comprise WSsoy at 10% weight and 1.5% polyethylene oxide. The flow rate of the soy-water mixture through the inner needle of the spinneret can be between 0.1 mL/hr and 5 ml/hr, as controlled by the pressure of the gas from cartridge regulators and valves. In some embodiments, the flow rate of soy-water mixture through the inner needle of the spinneret is 0.5 mL/hr. In some embodiments, the flow rate of soy-water mixture through the inner needle of the spinneret is 1.5 mL/hr. The pressure of gas delivered through the outer sheath of the spinneret can be controlled by a gas regulator to be between 1 and 60 psi. In some embodiments, the pressure of gas delivered through the outer sheath of the spinneret is 20 psi. In some embodiments, the pressure of gas delivered through the outer sheath of the spinneret is between 3 and 5 psi. In some embodiments, wherein a voltage is applied to the inner needle of the spinneret, the voltage can be between 1 and 30 kV. In certain embodiments, a 5 kV voltage is applied to the inner needle of the spinneret.

In some embodiments, the spinning solution may further comprise an additional polymer. Non-limiting examples of polymers include: polyurethane, polysiloxane or silicone, polyethylene, polyvinyl pyrrolidone (PVP), poly(2-hydroxy ethyl methacrylate), poly(N-vinyl pyrrolidone), polymethyl methacrylate, polyvinyl alcohol (PVA), polyacrylic acid, polyacrylamide, polyethylene-co-vinyl acetate, polyethylene glycol (PEG), polyethylene oxide (PEO), polymethacrylic acid, polylactide (PLA), polyglycolide (PGA), poly (lactic-co-glycolic acid) (PLGA), polystyrene, polyanhydride, polyorthoester, polycarbonate, and the like.

In some embodiments, the spinning solution may further comprise an additional therapeutic. Non-limiting examples of therapeutics include: anesthetics, antiallergics, antihistamines, antipruritics, muscle relaxants, analgesics, antipyretics, vitamins, antimicrobial agents, antiseptics, disinfectants, fungicides, ectoparasiticides, antiparasitics, alkaloids, salts, ions, anti-inflammatoireund healing agents, plant extracts, growth factors, polycarbonates, extracellular matrix (ECM) constituents such as ECM proteins, emollients, antibacterial or antiviral agents, tranquilizers, antitussives, nanoparticles such as silver ions, stem cells, epithelial cells, endothelial cells, and the like.

In some embodiments, the spinning solution may further comprise an additional animal or plant protein. Non-limiting examples include: gelatin, Matrigel, keratin, collagen, elastin, fibrin, hyaluronic acid, glycosaminoglycan, proteoglycan, fibronectin, vitronectin, laminin, chitosan, and soy-chitosan.

In some embodiments, resultant fabric is not irritating to the wound bed, is highly flexible, and is biodegradable, negating the need for removal and avoiding unnecessary debridement of the wound bed. Furthermore, the dispensed material is environmentally friendly and does not require any toxic solvents.

While most embodiments comprise rapid application of the spinning solution to a fresh wound, the methods of the present invention also encompass the fabrication of wound dressings beforehand. For example, prior to the incidence of a wound, the methods of the present invention may be performed on any surface, smooth or textured, to generate a non-woven fabric-like structure of any shape, size, thickness, or texture. The non-woven fabric-like structure may be removed from the target surface and kept for later use. In some embodiments, the fabric-like structure may be further treated after fabrication. For example, in one embodiment, the fabric-like structure may be treated in a vacuum oven after fabrication, wherein the vacuum oven treatment improves robustness and enables the fabric-like structure to remain in a nano-fibrous mesh for a longer period of time in aqueous conditions. Vacuum oven treatment also enables crosslinking without additional compounds, wherein the fabric-like structure slowly forms into a gel-like substance in water, while a non-crosslinked structure merely dissolves in water.

In other embodiments, the invention relates to methods for aerodynamically spinning any solution onto any substrate, such as for immediate covering, sealing, patching, or reinforcing the said intact or compromised substrates. While traditional spinning methods generally use a charged substrate in a controlled environment, the methods of the present invention use handheld EFBS devices to deposit spinning solutions onto charged and uncharged flat, textured, or 3D substrates in a variety of environments.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Atomization of Soy-Water Mixture for Use as a Portable Bandage Treatment Modified water-soluble purified soy protein isolates that have recently become available can be dissolved into solution and applied to a wound by spraying. In a simple context this can enable rapid application of a gel-like solution. However, with the inclusion of a second high-molecular weight polymer, such as polyethylene oxide (PEO), the atomized drops can dry into a fabric which can bandage a wound directly. Considering that the soy product has demonstrated wound healing efficacy in other contexts, this may enable a single step wound treatment option, one that both protects the wound and also hastens and enhances repair (Har-el, Y., Gerstenhaber, J. A., Brodsky, R., Huneke, R. B., and Lelkes, P. I. (2014) Electrospun soy protein scaffolds as wound dressings: Enhanced reepithelialization in a porcine model of wound healing, Wound Medicine 5, 9-15). While controlled nozzle design can allow for fabric formation spontaneously, in order to better coat the target wound, a high voltage (5 kV) is applied to the polymer stream in order to attract the fibers to the target (similar to the application of flocking). This has been accomplished using a handheld device electrofocused blow spinning device. Alternatively, the fabric can be prepared on a separate target using alternative forms of attraction (such as airflow) and then applied to the wound as a bandage, or cut to pieces and applied as traditional flocking.

Figure 7:
FIG. 7 depicts a sample of spinning solution dispensed on an appendage (outlined region) using a prototype handheld EFBS.
Figure 8:
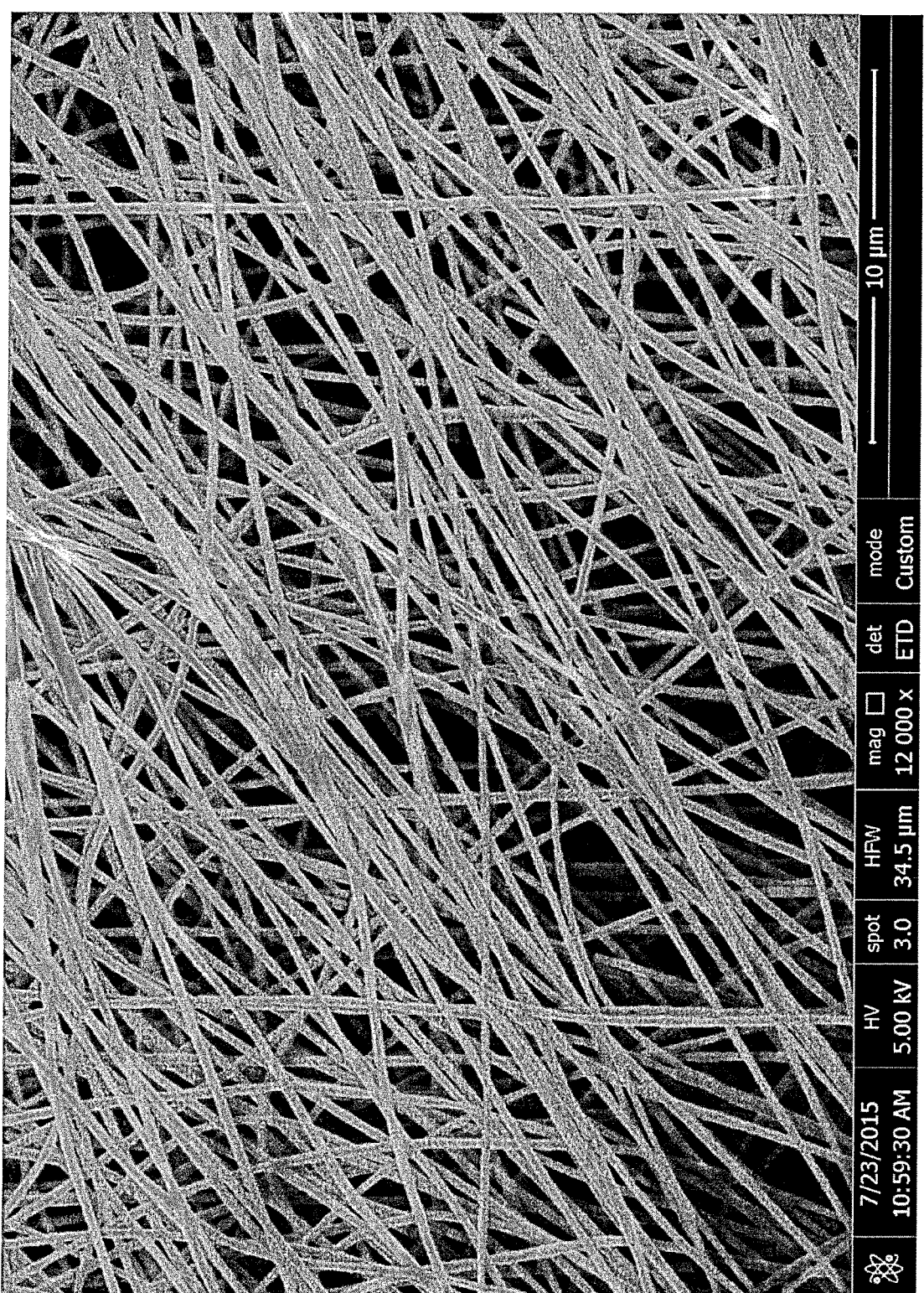
FIG. 8 depicts an SEM image of electrofocused blow spun fibers created by an exemplary EFBS using a composition comprising 8% water soluble soy.
Figure 9:
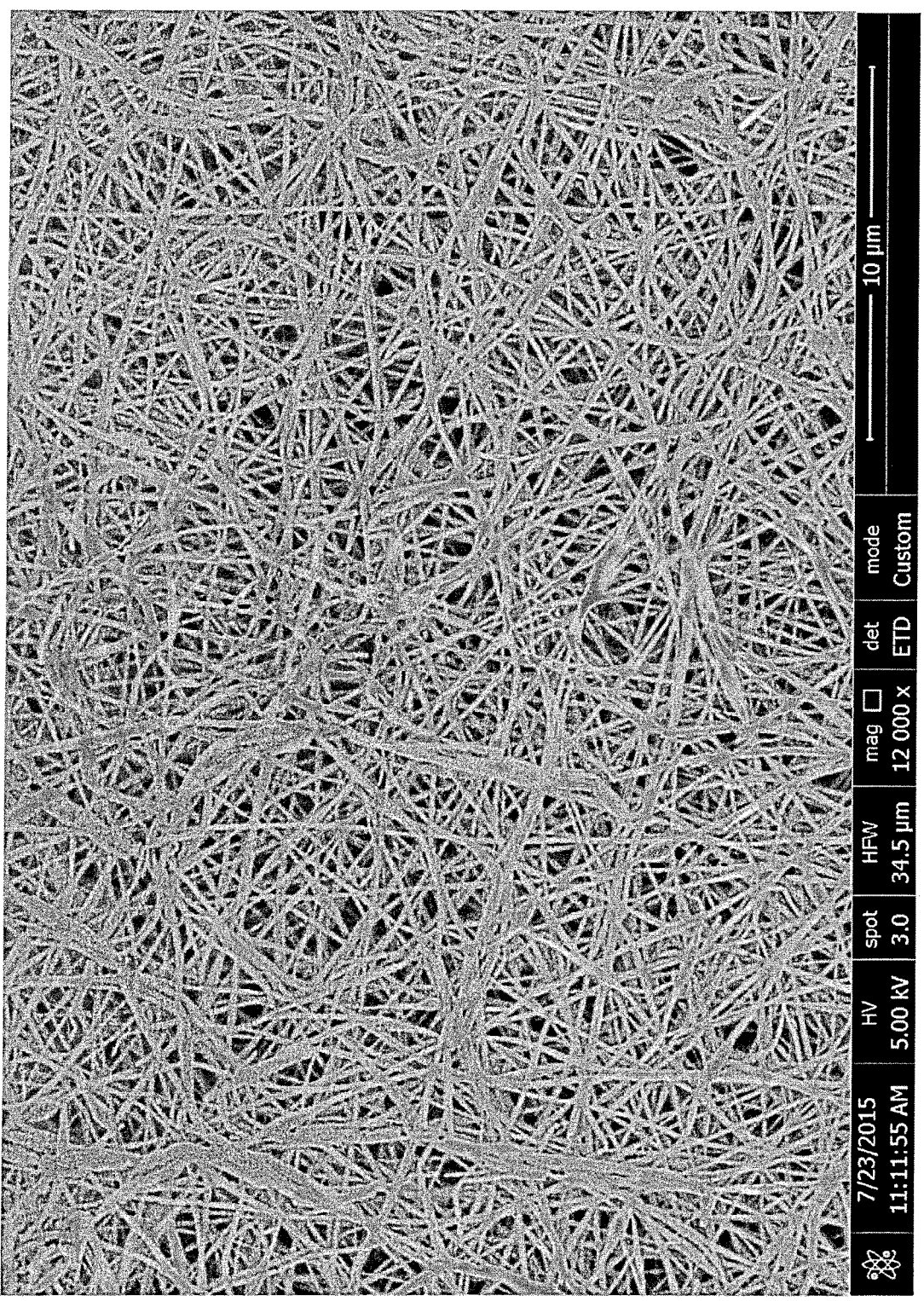
FIG. 9 depicts an SEM image of electrofocused blow spun fibers created by an exemplary EFBS using a composition comprising 8% water soluble soy after 24 hours heat treatment at 90° C. under vacuum.
Figure 10:
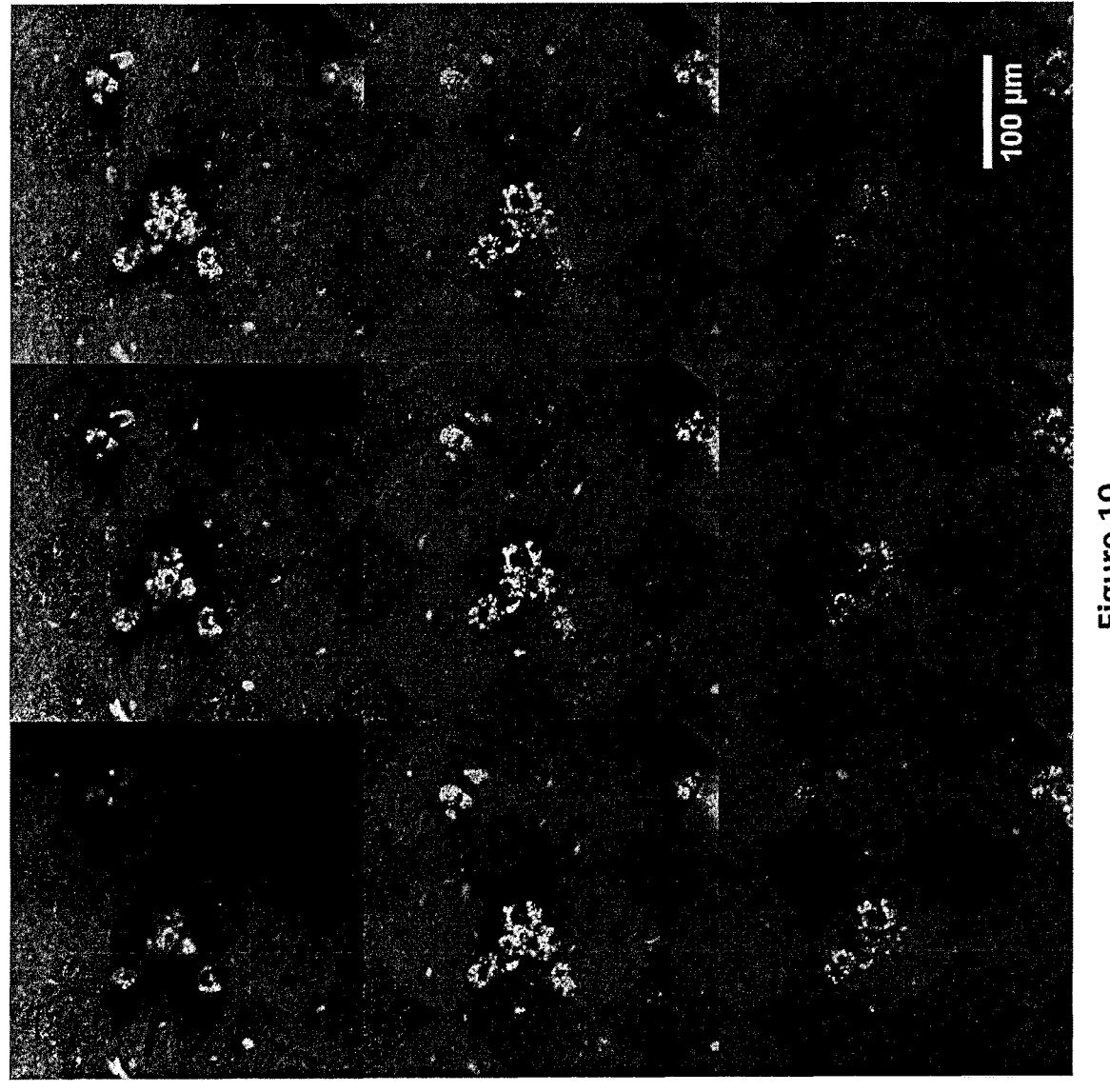
FIG. 10 depicts a series of images of A549 cells cultured on an electrofocused blow spun scaffold created by an exemplary EFBS. The images represent successive depths 2.4 µm apart. A549 cells are labeled with DiI dye seeded at low density after 3 days (10k cells in 48 well plate). The immediately adjacent to the cells is visibly broken down by the cells.
Figure 11:
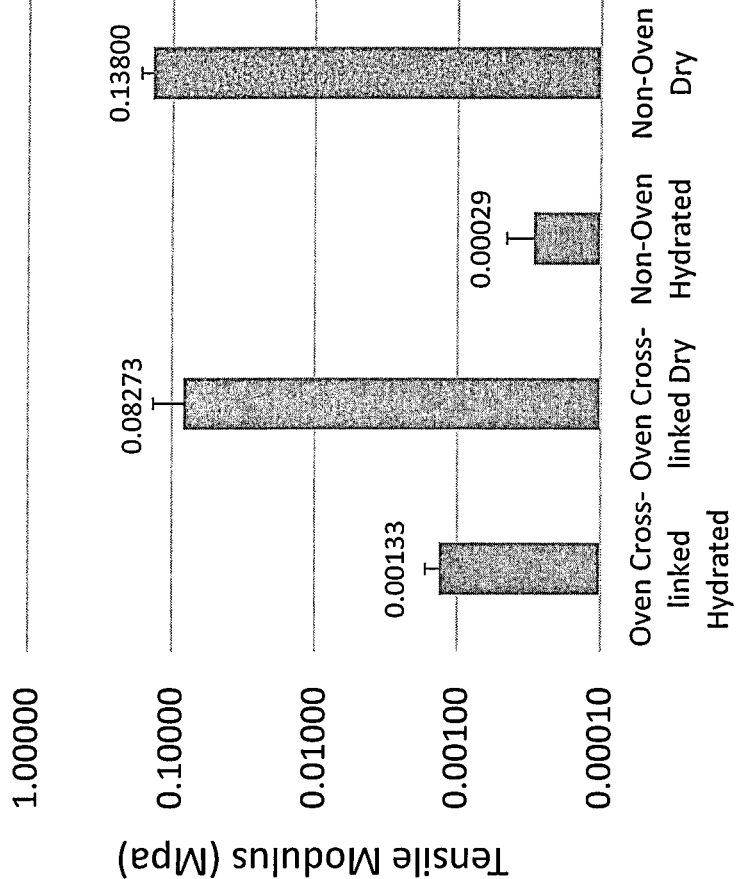
FIG. 11 depicts the effect of different post-blow spinning treatment on the tensile modulus of electrofocused blow-spun scaffolds.
Figure 12:
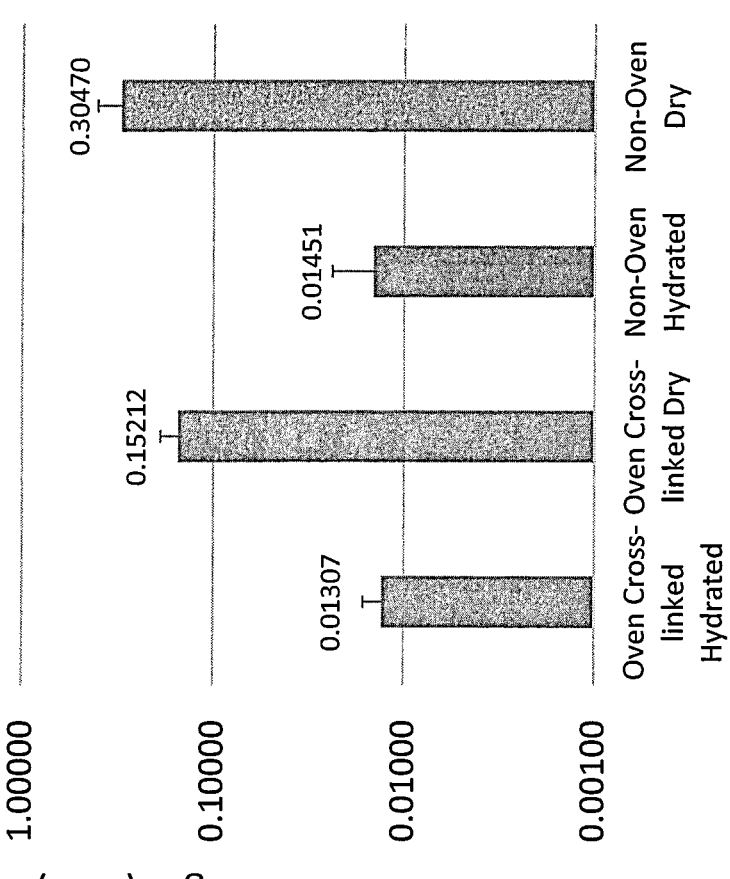
FIG. 12 depicts the effect of different post-blow spinning treatment on the ultimate tensile strength of electrofocused blow-spun scaffolds.

Dissolving water-soluble soy at a weight 10% with the addition of polyethylene oxide at 1.5%, a solution is produced that can be aerosolized or sprayed into fibers. In one embodiment, this solution is pushed through an external mix nozzle created from a central 30 gauge needle forming the inner lumen surrounded by a P100 pipette tip forming a narrow concentric lumen 1 mm behind the needle tip. Fluid is delivered to the central lumen at 0.5 ml/hr and gas is delivered to the outer lumen at 20 psi. The tip design only requires high shear forces at the tip of the needle. As such, the tight fit of the needle with the pipette tip allows fairly low airflow to enable fiber production. In the current embodiment, the airflow required is below the detection limit of the measuring device employed (<0.5 L/min). Upon leaving the nozzle, after 10 cm the spray is reduced to fibers of the soy material ranging (depending on the setup) from under 1 micron to a couple microns in diameter. A significantly sized fabric of ~250 micron thickness can be completed on bare skin in under 5 minutes (FIG. 7, outlined region).

Due to the airflow and the extremely low weight of the fibers, without further system modification the fibers will not deposit directly on a surface. Instead the fibers will blow around the surface. By using a needle as described, the airflow can be minimized, and by inducing a charge on the fibers after they are formed, the fibers can rapidly collect on the surface by electrostatic interaction. This has so far been accomplished by a high voltage/low amperage generator set to 5 kV. Fabrics have been formed without the use of the voltage source, but are built up more slowly on the target as most of the fabric tends to create a sort of veil around it due to aerodynamic forces.

In another embodiment, through the use of structured airflow, at minimum it should be possible to create fabrics on porous targets without the use of high voltage. As the device uses only moderate amounts of airflow and voltages that are easily generated in portable consumer devices (commonly in negative-ion air purifiers), the aerodynamic system can be assembled into a portable, lightweight, handheld apparatus. In its most primitive prototype state this system consists of a 16 g $CO_2$ cylinder with a pressure regulator outputting the 20 psi required for the soy atomization, a second low pressure regulator used to pump the soy fluid to the mix needle, and a 5k V high voltage power supply powered from a 9V battery. In a more advanced design, the entire system can be contained entirely in a purpose-made aerosol can.

The fabric can be best compared to electrospun fibers. Electrospun fibers have been demonstrated to be useful in wound healing applications due to the ability to use biodegradable materials with cell/ECM-relevant sizes (Frohbergh, M. E., Katsman, A., Botta, G. P., Lazarovici, P., Schauer, C. L., Wegst, U. G., and Lelkes, P. I. (2012) Electrospun hydroxyapatite-containing chitosan nanofibers crosslinked with genipin for bone tissue engineering, Biomaterials 33, 9167-9178; Frohbergh, M. E., Katsman, A., Mondrinos, M. J., Stabler, C. T., Hankenson, K. D., Oristaglio, J. T., and Lelkes, P. I. (2015) Osseointegrative properties of electrospun hydroxyapatite-containing nanofibrous chitosan scaffolds, Tissue Eng Part A 21, 970-981; Han, J., Lazarovici, P., Pomerantz, C., Chen, X., Wei, Y., and Lelkes, P. I. (2011) Co-electrospun blends of PLGA, gelatin, and elastin as potential nonthrombogenic scaffolds for vascular tissue engineering, Biomacromolecules 12, 399-408; Han, J., Farah, S., Domb, A. J., and Lelkes, P. I. (2013) Electrospun rapamycin-eluting polyurethane fibers for vascular grafts, Pharm Res 30, 1735-1748; Lelkes, P. I., Li, M., Perets, A., Lin, L., Han, J., and Woerdeman, D. L. (2008) Electrospinning of natural proteins for tissue engineering scaffolding, In Handbook of natural-based polymers for biomedical applications (Reis, R. L., Ed.), pp 446-482, Woodhead Publishing, Ltd., Cambridge, England; Li, M., Mondrinos, M. J., Gandhi, M. R., Ko, F. K., Weiss, A. S., and Lelkes, P. I. (2005) Electrospun protein fibers as matrices for tissue engineering, Biomaterials 26, 5999-6008; Lin, L., Perets, A., Har-cl, Y., Varma, D., Li, M., Lazarovici, P., Woerdeman, D. L., and Lelkes, P. I. (2013) Alimentary 'green' proteins as electrospun scaffolds for skin regenerative engineering, J Tissue Eng Regen Med 7, 994-1008). Unfortunately, the fibers are produced extremely slowly and, in most cases, require organic solvents that are harsh, expensive, and often quite toxic. Recently, a technique referred to as air spinning has taken the place of electrospinning. Air spinning of fabrics using traditional air-brush techniques directly onto organs has been demonstrated. However, the materials that can be airspun have so far been limited to artificial polymers rather than natural proteins, and still require solvents that can be hazardous for use directly in a biological environment; acetone, for example, being one of the safest solvents yet demonstrated. Although not leveraged here, electroblowing, a blend of air-spraying with high voltage necessary to induce fiber formation as in electrospinning, has also been introduced. While this has been demonstrated at low spinning rates using hyaluronic acid dissolved in water, fiber production in such a scenario has yet to demonstrate the quality managed here. In addition, the soy material used here has been demonstrated to have specific advantages in a skin wound model and has never been demonstrated elsewhere. Obvious primitive alternatives can also include liquid bandages which only provide a protective layer and lack the advantages of the cellular level microfibers.

The invention alleviates the need for electroprocessing in fiber generation; rather it provides for a simple, single application to enhance wound healing while protecting the wound bed. This can be accomplished in a mobile situation in a rapid manner enabling a conformal coating, especially of geometrically complex surfaces, that cannot be accomplished easily with pre-made bandages. It provides a fabric which is not irritating to the wound bed, is highly flexible, and does not need to be removed as it is biodegradable, avoiding unnecessary debridement of the wound bed. The fabric provided is environmentally friendly and does not require any toxic solvents during creation for either the operator or for the wound bed.

Applications of the device and method include, for example, first aid responder bandage application for large wounds (including burns); use at home as a bandaging device; and use in a hospital or chronic care setting for the bandaging of wounds.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A handheld electrofocused blow spinning (EFBS) device, comprising:
   a spinneret comprising an outer sheath and an inner needle;
   a syringe, configured to hold a spinning solution, fluidly connected to the spinneret inner needle;
   at least one gas regulator; and
   a single source of gas fluidly connected to the syringe via a first gas flow and the spinneret outer sheath via a second gas flow, such that the single source of gas is configured to simultaneously pressurize the syringe and propel gas out of the spinneret outer sheath.

2. The device of claim 1, wherein the inner needle is electrically conductive.

3. The device of claim 2, further comprising a power source and a power supply electrically connected to the inner needle.

4. The device of claim 3, wherein the source of gas comprises a pressurized cartridge of gas loadable into the at least one gas regulator.

5. The device of claim 4, further comprising a housing, wherein the housing at least partially encases the EFBS device and includes a slot for engaging and disengaging the pressurized cartridge of gas.

6. The device of claim 5, wherein the device further comprises at least one of a grip, a handle, a gripping portion.

7. The device of claim 6, wherein the gas is selected from the group consisting of CO2, N2, NO, and air.

8. The device of claim 7, wherein the outer sheath has a diameter ranging between 0.5 and 2.5 mm, and the inner needle has a gauge ranging between 20 and 30 gauge.

9. The device of claim 8, wherein the power supply produces an output ranging between 100V and 30 kV.

10. The device of claim 1, wherein the source of gas comprises an air pump.

11. The device of claim 10, wherein the pump is selected from the group consisting of a syringe pump, a peristaltic pump, a diaphragm pump, and a vane pump.

12. The device of claim 1, wherein the spinning solution comprises a plant protein, an animal protein, a synthetic polymer, or any combination thereof.

13. The device of claim 12, wherein the plant protein comprises water-soluble soy protein, or a bioactive component thereof.

14. The device of claim 13, wherein the spinning solution further comprises a polymer.

15. The device of claim 14, wherein the polymer is polyethylene oxide.

16. A handheld electrofocused blow spinning (EFBS) device, comprising:

a spinneret having an outer sheath and an inner needle;

a syringe fluidly connected to the spinneret inner needle;

a gas regulator fluidly connected to the syringe and spinneret, the gas regulator configured to engage a pressurized gas cartridge; and a first valve positioned between the gas regulator and the syringe, and a second valve positioned between the gas regulator and the spinneret.

17. The device of claim 16, wherein the inner needle comprises a non-conductive portion fluidly connected to a conductive portion.

18. The device of claim 17, wherein the nonconductive portion is fluidly connected to the conductive portion with a nonconductive tube, wherein the nonconductive tube is formed of at least one polymer material.

19. The device of claim 17, further comprising a power source and a power supply electrically connected to the conductive portion of the inner needle.

20. The device of claim 19, further comprising a housing at least partially encasing the EFBS device, the housing including at least one slot for engaging and disengaging the pressurized gas cartridge.

21. The device of claim 20, further comprising a digital display attached to the housing, and a plurality of flow sensors, pressure sensors and voltage sensors positioned inside the housing configured to provide sensor measurements from the EFBS device to the digital display.

22. The device of claim 16, wherein the device further comprises at least one of a grip, a handle, a gripping portion.

23. The device of claim 22, wherein the gas regulator is formed in the shape of a hand grip.

24. A handheld electrofocused blow spinning (EFBS) device, comprising:

a spinneret having an outer sheath and an inner needle;

a spinning solution container fluidly connected to the spinneret inner needle;

a gas regulator fluidly connected to the spinning solution container and spinneret;

a source of gas fluidly connected to the gas regulator; and a first valve positioned within a first flow path between the gas regulator and the syringe, and a second valve positioned within a second flow path between the gas regulator and the spinneret.

25. The device of claim 24, wherein the outer sheath is at least partially formed in the shape of a cone.

26. The device of claim 24, wherein the distance between the tip of the inner needle and the opening of the outer sheath is adjustable.

27. The device of claim 24, wherein the tip of the inner needle extends out 1 mm past the opening of the outer sheath.

\* \* \* \* \*